United States Patent [19]

Shiloh

[11] Patent Number: 5,756,288
[45] Date of Patent: May 26, 1998

US005756288A

[54] ATAXIA-TELANGIECTASAI GENE

[75] Inventor: Yosef Shiloh, Tel Aviv, Israel

[73] Assignee: Ramot-University of Authority for Applied Research and Industrial Dev. Ltd., Tel Aviv, Israel

[21] Appl. No.: 441,822

[22] Filed: May 16, 1995

[51] Int. Cl.$^6$ .............................. C12Q 1/68; C07H 21/04
[52] U.S. Cl. .......................... 435/6; 536/23.1; 536/23.2; 536/24.31
[58] Field of Search .............................. 435/6; 536/23.1, 536/24.31, 23.2

[56] References Cited

FOREIGN PATENT DOCUMENTS

| | | | |
|---|---|---|---|
| WO 9400572 | 1/1994 | WIPO | C12N 15/12 |
| WO 9503431 | 2/1995 | WIPO | C12Q 1/68 |

OTHER PUBLICATIONS

Rasio et al., (1995) "Genomic organization of the ATM locus involved in Ataxia–Telangiectasia" *Cancer Research*, 55:6053–6057.
Baumer et al. (1996) Hum. Genet. 98: 246–249.
Novak Science (1995 Jun. 23) 268 (5218): 1700–1.
Gilad et al. Hum Molecular Genet. (1996) 5(4): 433–439.
Wright et al. Am. J. Hum. Genet. (1996) 59: 839–846.
Kapp, "Cloning of a candidate gene for Ataxia–Telangiectasia Group D" *Am. J. Hum. Genet.*, 51:45–54 (1992).
Leonardt et al., "Nucleotide sequence analysis of a candidate gene for Ataxia–Telangiectasia Group D (ATDC)" *Genomics*, 19:130–136 (1994).
Aksentijevitch et al. "Familial Mediterranean fever in Moroccan Jews: demonstration of a founder effect by extended haplotype analysis" *Am. J. Hum. Genet.*, 53:644–651 (1993).
Ambrose et al., "A physical map across chromosome 11q22–23 containing the major locus for ataxia–telangiectasia" *Genomics*, 21:612–619 (1994).
Attree et al., "The Lowe's oculocerebrorenal syndrome gene encodes a protein highly homologous to inositol . . . " *Nature*, 358:239–242 (1992).
Beamish and Lavin, "Radiosensitivity in ataxia–telangiectasia: anomalies in radiation–induced cell cycle delay" *J. Radiat. Biol.*, 65:175–184.
Berger et al., "Isolation of a candidate gene for Norrie disease by positional cloning" *Nature Genet.* 1:199–203 (1992).
Buckler et al., "Exon amplification: a strategy to isolate mammalian genes used on RNA splicing" *Proc. Natl. Acad. Sci. USA*, 88:4005–4009 (1991).
Chakravarti et al., "Nonuniform recombination within the human beta–globin gene cluster" *Am. J. Hum. Genet.*, 36:1239–1258 (1984).
Chelly et al., "Isolation of a candidate gene for Menkes disease that encodes a potential heavy metal binding protein" *Nature Genet.*, 3:14–19 (1993).
Church et al., "Isolation of genes from complex sources of mammalian genomic DNA using exon amplification" *Nature Genet.*, 6:98–104 (1993).

Collins, "Positional cloning: let's not call it reverse anymore" *Nature Genet.*, 1:3–6 (1992).
Duyk et al., "Exon trapping: a genetic screen to identify candidate transcribed sequences in cloned mammalian genomic DNA" *Proc. Natl. Acad. Sci. USA*, 87:8995–8999 (1990).
Foroud et al., "Localization of the AT locus to an 8 cM interval defined by STMY and S132" *Am. J. Hum. Genet.*, 49:1263–1279 (1991).
Frohman, PCR Methods and Applications, 4:S40–S58 (1994).
Frohman et al., *Proc. Natl. Sci. USA*, 85:8998–9002 (1988).
Gatti et al., "Genetic haplotyping of ataxia–telangiectasia families localizes the major gene to an 850 kb region on chromosome . . . " *Int. J. Radiat. Biol.*, (in press) (1994).
Gatti et al., "Localization of an ataxia–telangiectasia gene to chromosome 11q22–23" *Nature*, 336:577–580 (1988).
Morgan et al., "The selective isolation of novel cDNAs encoded by the regions surrounding the human interleukin 4 and 5 genes" *Nucleic Acids Res.*, 20:5173–5179 (1992).
Oskato et al., "Ataxia–telangiectasia: allelic association with 11q22–23 markers in Moroccan–Jewish patients" *43rd Annual Meeting of the American Society of Human Genetics*, New Orleans, LA (1993).
Ozelius et al., "Strong allelic association between the torsion dystonia gene (DYT1) and loci on chromosome . . . " *Am. J. Hum. Genet.*, 50:619–628 (1992).
Parimoo et al., "cDNA selection: efficient PCR approach for the selection of cDNAs encoded in large chromosomal DNA fragments" *Proc. Natl. Acad. Sci. USA*, 88:9623–9627 (1991).
Rotman et al., "Rapid identification of polymorphic CA–repeats in YAC clones" *Molecular Biotechnology* (in press) (1994a).
Rotman et al., "Three dinucleotide repeat polymorphisms at the ataxia–telangiectasia locus" *Human Molecular Genetics* (in press) (1994b).
Rotman et al., "A YAC contig spanning the ataxia–telangiectasia locus (groups A and C) on chromosome 11q22–23" *Genomics* (in press) (1994c).
Rotman et al., "Physical and genetic mapping of the ATA/ATC locus in chromosome 11q22–23" *Int. J. Radiat. Biol.* (in press) (1994d).

(List continued on next page.)

*Primary Examiner*—Lisa B. Arthur
*Attorney, Agent, or Firm*—Kohn & Associates

[57] ABSTRACT

A purified, isolated and cloned DNA sequence consisting essentially of a DNA sequence (SEQ ID No:1) partially encoding the gene, designated ATM, mutations in which cause ataxia-telangiectasia and a method for detecting carriers of the defective gene which causes ataxia-telangiectasia. The method includes isolating genetic material from a cell sample of a subject and the genetic material with molecular probes complementary to SEQ ID No:1 and point mutations, deletions or insertions thereof in order to detect carriers of the mutant gene.

21 Claims, 1 Drawing Sheet

OTHER PUBLICATIONS

Savitsky et al., "A single gene with homologies to phosphatidylinositol 3-kinases and rad3+ is mutated in all . . . " (submitted for publication).

Sirugo et al., "Friedreich ataxia in Louisiana Acadians: demonstration of a founder effect by analysis . . . " *Am. J. Hum. Genet.,* 50:559–566 (1992).

Shiloh, "Ataxia-telangiectasia: closer to unraveling the mystery" *European Journal of Human Genetics* (in press).

Shiloh et al., "Carrier detection in ataxia-telangiectasia" *The Lancet,* I:689 (1986).

Swift et al., "Cancer predisposition of ataxia-telangiectasia heterozygotes" *Cancer Genet, Cytogenet.,* 46:21–27 (1990).

Hastbacka et al., "Linkage dissequilibrium mapping in isolated founder populations: diastrophic dysplasia in Finland" *Nature Genet.,* 2:204–211 (1992).

Heim et al., "Heterozygous manifestations in four autosomal recessive human cancer-prone syndromes . . . " *Mutat. Res.,* 284:25–36 (1992).

Kastan et al., "A mammalian cell cycle checkpoint pathway utilizing p53 and GADD45 is defective in ataxia-telangiectasia" *Cell,* 71:587–597.

Kerem et al., "Identification of the cystic fibrosis gene: genetic analysis" *Science,* 245:1073–1080 (1989).

Khanna and Lavin, "Ionizing radiation and UV induction of p53 protein by different pathways in ataxia-telangiectasia cells" *Oncogene,* 8:3307–3312 (1993).

Lange et al., "Localization of an ataxia-telangiectasia gene to a 850 kb interval on chromosome 11q23.1 by linkage . . . " (submitted) (1994).

Lehesjoki et al., Localization of the EPM1 gene for progressive myoclonus epilepsy on chromosome 21: linkage disequilibrium . . . *Hum. Mol. Genet.,* 2:1229–1234 (1993).

Litt and Luty, "A hypervariable microsatellite revealed by in vitro amplification of a dinucleotide repeat within the cardiac muscle . . . " *Am. J. Hum. Genet.,* 44:397–401 (1989).

Llerena et al., "Spontaneous and induced chromosome breakage in chorionic villus samples . . . " *J. Med. Genet.,* 26:174–178 (1989).

McConville et al., "Genetic and physical mapping of the ataxia-telangiectasia locus on chromosome 11q22–23" *Int. J. Radiat. Biol.* (in press) (1994).

McConville et al., *Hum. Mol. Genet.,* 2:969–974 (1993).

McConville et al., *Nucleic Acids, Res.,* 18:4335–4343 (1990).

Miki et al., "A strong candidate for the breast and ovarian cancer susceptibility gene BRCA1" *Science,* 266:66–71 (1994).

Mitchison et al., "Fine genetic mapping of the Batten Disease locus (CLN3) by haplotype analysis and demonstration . . . " *Genomics,* 16:455–460 (1993).

Swift et al., "Incidence of cancer in 1616 families affected by ataxia-telangiectasia" *New Engl. J. Med.,* 325:1831–1836 (1991).

Tagle et al., "Magnetic bead capture of expressed sequences encoded within large genomic segments" *Nature,* 361:751–753 (1993).

The European Polycystic Kidney Disease Consortium, "The polycystic kidney disease 1 gene encodes a 14 kb transcript . . . " *Cell,* 77:881–894 (1994).

The Huntington's Disease Collaborative Research Group, "A novel gene containing a trinucleotide repeat that is expanded . . . " *Cell,* 72:971–983 (1993).

Trofatter et al., "A novel moesin-, ezrin-, radixin-like gene is a. candidate for the neurofibromatosis 2 tumor suppressor" *Cell,* 72:791–800 (1993).

Vanagaite et al., "Physical localization of microsatellite markers at the ataxia-telangiectasia locus at 11q22–23" *Genomics,* 22:231–233 (1994a).

Vanagaite et al., "A high-density microsatellite map of the ataxia-telangiectasia locus" *Human Genetics* (in press) (1994b).

Vetrie et al., "The gene involved in X-linked agammaglobulinemia is a member of the src family of protein-tyrosine kinases" *Nature,* 361:226–233 (1993).

Weber and May, "Abundant class of human DNA polymorphisms which can be typed using the polymerase chain reaction" *Am. J. Hum. Genet.,* 44:388–396 (1989).

Ziv et al., "Ataxia-telangiectasia: linkage analysis in highly inbred Arab and Druze families and differentiation . . ." *Hum. Genet.,* 88:619–626 (1992).

Ziv et al., "The ATC (ataxia-telangiectasia complementation group C) locus localizes to 11q22–q23" *Genomics,* 9:373–375 (1991).

Porter et al., "A novel selection system for recombinational and mutational events within an intron of a eucaryotic gene" *Nucleic Acids Research,* vol. 1 , No. 17, pp. 5173–5179 (1990).

Fig-1

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 7408 base pairs
( B ) TYPE: nucleic acid
( C ) STRANDEDNESS: single
( D ) TOPOLOGY: linear ( x i ) SEQUENCE DESCRIPTION: SEQ ID NO:1:

```
CGACAAATGA GGAATTCAGA ATTGGTTCCT TGAGAAATAT GATGCAGCTA TGTACACGTT      60

GCTTGAGCAA CTGTACCAAG AAGAGTCCAA ATAAGATTGC ATCTGGCTTT TTCCTGCGAT     120

TGTTAACATC AAAGCTAATG AATGACATTG CAGATATTTG TAAAAGTTTA GCATCCTTCA     180

TCAAAAAGCC ATTTGACCGT GGAGAAGTAG AATCAATGGA AGATGATACT AATGGAAATC     240

TAATGGAGGT GGAGGATCAG TCATCCATGA ATCTATTTAA CGATTACCCT GATAGTAGTG     300

TTAGTGATGC AAACGAACCT GGAGAGAGCC AAAGTACCAT AGGTGCCATT AATCCTTTAG     360
```

-continued

```
CTGAAGAATA TCTGTCAAAG CAAGATCTAC TTTCTTAGA  CATGCTCAAG TTCTTGTGTT    420
TGTGTGTAAC TACTGCTCAG ACCAATACTG TGTCCTTTAG GGCAGCTGAT ATTCGGAGGA    480
AATTGTTAAT GTTAATTGAT TCTAGCACGC TAGAACCTAC CAAATCCCTC CACCTGCATA    540
TGTATCTAAT GCTTTTAAAG GAGCTTCCTG GAGAAGAGTA CCCCTTGCCA ATGGAAGATG    600
TTCTTGAACT TCTGAAACCA CTATCCAATG TGTGTTCTTT GTATCGTCGT GACCAAGATG    660
TTTGTAAAAC TATTTTAAAC CATGTCCTTC ATGTAGTGAA AAACCTAGGT CAAAGCAATA    720
TGGACTCTGA GAACACAAGG GATGCTCAAG GACAGTTTCT TACAGTAATT GGAGCATTTT    780
GGCATCTAAC AAAGGAGAGG AAATATATAT TCTCTGTAAG AATGGCCCTA GTAAATTGCC    840
TTAAAACTTT GCTTGAGGCT GATCCTTATT CAAATGGGC  CATTCTTAAT GTAATGGGAA    900
AAGACTTTCC TGTAAATGAA GTATTTACAC AATTTCTTGC TGACAATCAT CACCAAGTTC    960
GCATGTTGGC TGCAGAGTCA ATCAATAGAT TGTTCCAGGA CACGAAGGGA GATTCTTCCA   1020
GGTTACTGAA AGCACTTCCT TTGAAGCTTC AGCAACAGC  TTTTGAAAAT GCATACTTGA   1080
AAGCTCAGGA AGGAATGAGA GAAATGTCCC ATAGTGCTGA GAACCCTGAA ACTTTGGATG   1140
AAATTTATAA TAGAAAATCT GTTTTACTGA CGTTGATAGC TGTGGTTTTA TCCTGTAGCC   1200
CTATCTGCGA AAAACAGGCT TTGTTTGCCC TGTGTAAATC TGTGAAAGAG AATGGATTAG   1260
AACCTCACCT TGTGAAAAAG GTTTTAGAGA AAGTTTCTGA ACTTTTGGA  TATAGACGTT   1320
TAGAAGACTT TATGGCATCT CATTTAGATT ATCTGGTTTT GGAATGGCTA AATCTTCAAG   1380
ATACTGAATA CAACTTATCT TCTTTTCCTT TTATTTATT  AAACTACACA AATATTGAGG   1440
ATTTCTATAG ATCTTGTTAT AAGGTTTTGA TTCCACATCT GGTGATTAGA AGTCATTTTG   1500
ATGAGGTGAA GTCCATTGCT AATCAGATTC AAGAGGACTG GAAAAGTCTT CTAACAGACT   1560
GCTTTCCAAA GATTCTTGTA AATATTCTTC CTTATTTGC  CTATGAGGGT ACCAGAGACA   1620
GTGGGATGGC ACAGCAAAGA GAGACTGCTA CCAAGGTCTA TGATATGCTT AAAAGTGAAA   1680
ACTTATTGGG AAAACAGATT GATCACTTAT TCATTAGTAA TTACCAGAG  ATTGTGGTGG   1740
AGTTATTGAT GACGTTACAT GAGCCAGCAA ATTCTAGTGC CAGTCAGAGC ACTGACCTCT   1800
GTGACTTTTC AGGGGATTTG GATCCTGCTC CTAATCCACC TCATTTTCCA TCGCATGTGA   1860
TTAAAGCAAC ATTTGCCTAT ATCAGCAATT GTCATAAAAC CAAGTTAAAA AGCATTTTAG   1920
AAATTCTTTC CAAAAGCCCT GATTCCTATC AGAAAATTCT TCTTGCCATA TGTGAGCAAG   1980
CAGCTGAAAC AAATAATGTT TATAAGAAGC ACAGAATTCT TAAATATAT  CACCTGTTTG   2040
TTAGTTTATT ACTGAAAGAT ATAAAAGTG  GCTTAGGAGG AGCTTGGGCC TTTGTTCTTC   2100
GAGACGTTAT TTATACTTTG ATTCACTATA TCAACCAAAG GCCTTCTTGT ATCATGGATG   2160
TGTCATTACG TAGCTTCTCC CTTTGTTGTG ACTTATTAAG TCAGGTTTGC CAGACAGCCG   2220
TGACTTACTG TAAGGATGCT CTAGAAAACC ATCTTCATGT TATTGTTGGT ACACTTATAC   2280
CCCTTGTGTA TGAGCAGGTG GAGGTTCAGA ACAGGTATT  GGACTTGTTG AAATACTTAG   2340
TGATAGATAA CAAGGATAAT GAAAACCTCT ATATCACGAT TAAGCTTTTA GATCCTTTTC   2400
CTGACCATGT TGTTTTTAAG GATTTGCGTA TTACTCAGCA AAAAATCAAA TACAGTAGAG   2460
GACCCTTTTC ACTCTTGGAG GAAATTAACC ATTTTCTCTC AGTAAGTGTT TATGATGCAC   2520
TTCCATTGAC AAGACTTGAA GGACTAAAGG ATCTTCGAAG ACAACTGGAA CTACATAAAG   2580
ATCAGATGGT GGACATTATG AGAGCTTCTC AGGATAATCC GCAAGATGGG ATTATGGTGA   2640
AACTAGTTGT CAATTTGTTG CAGTTATCCA AGATGGCAAT AAACCACACT GGTGAAAAAG   2700
AAGTTCTAGA GGCTGTTGGA AGCTGCTTGG GAGAAGTGGG TCCTATAGAT TTCTCTACCA   2760
```

-continued

| | | | | | |
|---|---|---|---|---|---|
| TAGCTATACA | ACATAGTAAA | GATGCATCTT | ATACCAAGGC | CCTTAAGTTA | TTTGAAGATA | 2820 |
| AAGAACTTCA | GTGGACCTTC | ATAATGCTGA | CCTACCTGAA | TAACACACTG | GTAGAAGATT | 2880 |
| GTGTCAAAGT | TCGATCAGCA | GCTGTTACCT | GTTTGAAAAA | CATTTTAGCC | ACAAAGACTG | 2940 |
| GACATAGTTT | CTGGGAGATT | TATAAGATGA | CAACAGATCC | AATGCTGGCC | TATCTACAGC | 3000 |
| CTTTTAGAAC | ATCAAGAAAA | AAGTTTTTAG | AAGTACCCAG | ATTTGACAAA | GAAAACCCTT | 3060 |
| TTGAAGGCCT | GGATGATATA | AATCTGTGGA | TTCCTCTAAG | TGAAAATCAT | GACATTTGGA | 3120 |
| TAAAGACACT | GACTTGTGCT | TTTTTGGACA | GTGGAGGCAC | AAAATGTGAA | ATTCTTCAAT | 3180 |
| TATTAAAGCC | AATGTGTGAA | GTGAAAACTG | ACTTTGTCA | GACTGTACTT | CCATACTTGA | 3240 |
| TTCATGATAT | TTTACTCCAA | GATACAAATG | AATCATGGAG | AAATCTGCTT | TCTACACATG | 3300 |
| TTCAGGGATT | TTTCACCAGC | TGTCTTCGAC | ACTTCTCGCA | AACGAGCCGA | TCCACAACCC | 3360 |
| CTGCAAACTT | GGATTCAGAG | TCAGAGCACT | TTTTCCGATG | CTGTTTGGAT | AAAAAATCAC | 3420 |
| AAAGAACAAT | GCTTGCTGTT | GTGGACTACA | TGAGAAGACA | AAAGAGACCT | TCTTCAGGAA | 3480 |
| CAATTTTTAA | TGATGCTTTC | TGGCTGGATT | TAAATTATCT | AGAAGTTGCC | AAGGTAGCTC | 3540 |
| AGTCTTGTGC | TGCTCACTTT | ACAGCTTTAC | TCTATGCAGA | AATCTATGCA | GATAAGAAAA | 3600 |
| GTATGGATGA | TCAAGAGAAA | AGAAGTCTTG | CATTTGAAGA | AGGAAGCCAG | AGTACAACTA | 3660 |
| TTTCTAGCTT | GAGTGAAAAA | AGTAAAGAAG | AAACTGGAAT | AAGTTTACAG | GATCTTCTCT | 3720 |
| TAGAAATCTA | CAGAAGTATA | GGGGAGCCAG | ATAGTTTGTA | TGGCTGTGGT | GGAGGGAAGA | 3780 |
| TGTTACAACC | CATTACTAGA | CTACGAACAT | ATGAACACGA | AGCAATGTGG | GGCAAAGCCC | 3840 |
| TAGTAACATA | TGACCTCGAA | ACAGCAATCC | CCTCATCAAC | ACGCCAGGCA | GGAATCATTC | 3900 |
| AGGCCTTGCA | GAATTTGGGA | CTCTGCCATA | TTCTTTCCGT | CTATTTAAAA | GGATTGGATT | 3960 |
| ATGAAAATAA | AGACTGGTGT | CCTGAACTAG | AAGAACTTCA | TTACCAAGCA | GCATGGAGGA | 4020 |
| ATATGCAGTG | GGACCATTGC | ACTTCCGTCA | GCAAAGAAGT | AGAAGGAACC | AGTTACCATG | 4080 |
| AATCATTGTA | CAATGCTCTA | CAATCTCTAA | GAGACAGAGA | ATTCTCTACA | TTTTATGAAA | 4140 |
| GTCTCAAATA | TGCCAGAGTA | AAAGAAGTGG | AAGAGATGTG | TAAGCGCAGC | CTTGAGTCTG | 4200 |
| TGTATTCGCT | CTATCCCACA | CTTAGCAGGT | TGCAGGCCAT | TGGAGAGCTG | GAAAGCATTG | 4260 |
| GGGAGCTTTT | CTCAAGATCA | GTCACACATA | GACAACTCTC | TGAAGTATAT | ATTAAGTGGC | 4320 |
| AGAAACACTC | CCAGCTTCTC | AAGGACAGTG | ATTTTAGTTT | TCAGGAGCCT | ATCATGGCTC | 4380 |
| TACGCACAGT | CATTTTGGAG | ATCCTGATGG | AAAAGGAAAT | GGACAACTCA | CAAAGAGAAT | 4440 |
| GTATTAAGGA | CATTCTCACC | AAACACCTTG | TAGAACTCTC | TATACTGGCC | AGAACTTTCA | 4500 |
| AGAACACTCA | GCTCCCTGAA | AGGGCAATAT | TTCAAATTAA | ACAGTACAAT | TCAGTTAGCT | 4560 |
| GTGGAGTCTC | TGAGTGGCAG | CTGGAAGAAG | CACAAGTATT | CTGGGCAAAA | AAGGAGCAGA | 4620 |
| GTCTTGCCCT | GAGTATTCTC | AAGCAAATGA | TCAAGAAGTT | GGATGCCAGC | TGTGCAGCGA | 4680 |
| ACAATCCCAG | CCTAAAACTT | ACATACACAG | AATGTCTGAG | GGTTTGTGGC | AACTGGTTAG | 4740 |
| CAGAAACGTG | CTTAGAAAAT | CCTGCGGTCA | TCATGCAGAC | CTATCTAGAA | AAGGCAGTAG | 4800 |
| AAGTTGCTGG | AAATTATGAT | GGAGAAAGTA | GTGATGAGCT | AAGAAATGGA | AAAATGAAGG | 4860 |
| CATTTCTCTC | ATTAGCCCGG | TTTTCAGATA | CTCAATACCA | AAGAATTGAA | AACTACATGA | 4920 |
| AATCATCGGA | ATTTGAAAAC | AAGCAAGCTC | TCCTGAAAAG | AGCCAAAGAG | GAAGTAGGTC | 4980 |
| TCCTTAGGGA | ACATAAAATT | CAGACAAACA | GATACACAGT | AAAGGTTCAG | CGAGAGCTGG | 5040 |
| AGTTGGATGA | ATTAGCCCTG | CGTGCACTGA | AAGAGGATCG | TAAACGCTTC | TTATGTAAAG | 5100 |
| CAGTTGAAAA | TTATATCAAC | TGCTTATTAA | GTGGAGAAGA | ACATGATATG | TGGGTATTCC | 5160 |

```
GGCTTTGTTC  CCTCTGGCTT  GAAAATTCTG  GAGTTTCTGA  AGTCAATGGC  ATGATGAAGA   5220
GAGACGGAAT  GAAGATTCCA  ACATATAAAT  TTTTGCCTCT  TATGTACCAA  TTGGCTGCTA   5280
GAATGGGGAC  CAAGATGATG  GGAGGCCTAG  GATTTCATGA  AGTCCTCAAT  AATCTAATCT   5340
CTAGAATTTC  AATGGATCAC  CCCCATCACA  CTTGTTTAT   TATACTGGCC  TTAGCAAATG   5400
CAAACAGAGA  TGAATTTCTG  ACTAAACCAG  AGGTAGCCAG  AAGAAGCAGA  ATAACTAAAA   5460
ATGTGCCTAA  ACAAAGCTCT  CAGCTTGATG  AGGATCGAAC  AGAGGCTGCA  AATAGAATAA   5520
TATGTACTAT  CAGAAGTAGG  AGACCTCAGA  TGGTCAGAAG  TGTTGAGGCA  CTTTGTGATG   5580
CTTATATTAT  ATTAGCAAAC  TTAGATGCCA  CTCAGTGGAA  GACTCAGAGA  AAAGGCATAA   5640
ATATTCCAGC  AGACCAGCCA  ATTACTAAAC  TTAAGAATTT  AGAAGATGTT  GTTGTCCCTA   5700
CTATGGAAAT  TAAGGTGGAC  CACACAGGAG  AATATGGAAA  TCTGGTGACT  ATACAGTCAT   5760
TTAAAGCAGA  ATTTCGCTTA  GCAGGAGGTG  TAAATTTACC  AAAAATAATA  GATTGTGTAG   5820
GTTCCGATGG  CAAGGAGAGG  AGACAGCTTG  TTAAGGGCCG  TGATGACCTG  AGACAAGATG   5880
CTGTCATGCA  ACAGGTCTTC  CAGATGTGTA  ATACATTACT  GCAGAGAAAC  ACGGAAACTA   5940
GGAAGAGGAA  ATTAACTATC  TGTACTTATA  AGGTGGTTCC  CCTCTCTCAG  CGAAGTGGTG   6000
TTCTTGAATG  GTGCACAGGA  ACTGTCCCCA  TTGGTGAATT  TCTTGTTAAC  AATGAAGATG   6060
GTGCTCATAA  AAGATACAGG  CCAAATGATT  TCAGTGCCTT  TCAGTGCCAA  AAGAAAATGA   6120
TGGAGGTGCA  AAAAAAGTCT  TTTGAAGAGA  AATATGAAGT  CTTCATGGAT  GTTTGCCAAA   6180
ATTTTCAACC  AGTTTTCCGT  TACTTCTGCA  TGGAAAAATT  CTTGGATCCA  GCTATTTGGT   6240
TTGAGAAGCG  ATTGGCTTAT  ACGCGCAGTG  TAGCTACTTC  TTCTATTGTT  GGTTACATAC   6300
TTGGACTTGG  TGATAGACAT  GTACAGAATA  TCTTGATAAA  TGAGCAGTCA  GCAGAACTTG   6360
TACATATAGA  TCTAGGTGTT  GCTTTTGAAC  AGGGCAAAAT  CCTTCCTACT  CCTGAGACAG   6420
TTCCTTTTAG  ACTCACCAGA  GATATTGTGG  ATGGCATGGG  CATTACGGGT  GTTGAAGGTG   6480
TCTTCAGAAG  ATGCTGTGAG  AAAACCATGG  AAGTGATGAG  AAACTCTCAG  GAAACTCTGT   6540
TAACCATTGT  AGAGGTCCTT  CTATATGATC  CACTCTTTGA  CTGGACCATG  AATCCTTTGA   6600
AAGCTTTGTA  TTTACAGCAG  AGGCCGGAAG  ATGAAACTGA  GCTTCACCCT  ACTCTGAATG   6660
CAGATGACCA  AGAATGCAAA  CGAAATCTCA  GTGATATTGA  CCAGAGTTTC  GACAAAGTAG   6720
CTGAACGTGT  CTTAATGAGA  CTACAAGAGA  AACTGAAAGG  AGTGGAAGAA  GGCACTGTGC   6780
TCAGTGTTGG  TGGACAGGTG  AATTTGCTCA  TACAGCAGGC  CATAGACCCC  AAAAATCTCA   6840
GCCGACTTTT  CCCAGGATGG  AAAGCTTGGG  TGTGATCTTC  AGTATATGAA  TTACCCTTTC   6900
ATTCAGCCTT  TAGAAATTAT  ATTTTAGCCT  TTATTTTTAA  CCTGCCAACA  TACTTTAAGT   6960
AGGGATTAAT  ATTTAAGTGA  ACTATTGTGG  GTTTTTTTGA  ATGTTGGTTT  TAATACTTGA   7020
TTTAATCACC  ACTCAAAAAT  GTTTGATGG   TCTTAAGGAA  CATCTCTGCT  TTCACTCTTT   7080
AGAAATAATG  GTCATTCGGG  CTGGGCGCAG  CGGCTCACGC  CTGTAATCCC  AGCACTTTGG   7140
GAGGCCGAGG  TGAGCGGATC  ACAAGGTCAG  GAGTTCGAGA  CCAGCCTGGC  CAAGAGACCA   7200
GCCTGGCCAG  TATGGTGAAA  CCCTGTCTCT  ACTAAAAATA  CAAAAATTAG  CCGAGCATGG   7260
TGGCGGGCAC  CTGTAGTCCC  AGCTACTCGA  GAGGCTGAGG  CAGGAGAATC  TCTTGAACCT   7320
GGGAGGTGAA  GGTTGCTGTG  GGCCAAAATC  ATGCCATTGC  ACTCCAGCCT  GGGTGACAAG   7380
AGCGAAACTC  CATCTCAAAA  AAAAAAA                                          7408
```

ATAXIA-TELANGIECTASAI GENE

GRANT SUPPORT

This work was supported in part by grants from the National Institutes of Health, U.S.-Israel Binational Science Foundation, A-T Medical Research Foundation, A-T Medical Trust, and the A-T Children's Project.

TECHNICAL FIELD

The present invention relates to the isolation of the defective gene which causes ataxia-telangiectasia (A-T), designated ATM, and the use of the defective gene in detection of carriers of the A-T gene, and preparing native and transgenic organisms in which the gene products encoded by the ATM gene are artificially produced, or the expression of the native ATM gene is modified.

BACKGROUND OF THE INVENTION

Ataxia-telangiectasia (A-T) is a progressive genetic disorder affecting the central nervous and immune systems, and involving chromosomal instability, cancer predisposition, radiation sensitivity, and cell cycle abnormalities. Studies of the cellular phenotype of A-T have pointed to a defect in a putative system that processes a specific type of DNA damage and initiates a signal transduction pathway controlling replication and repair. For a general review of Ataxia-telangiectasia, reference is hereby made to the review *Ataxia-Telangiectasis: Closer to Unraveling the Mystery*, Eur. J. Hum. Genet. (in press) which, along with its cited references, is hereby incorporated by reference.

Despite extensive investigation over the last two decades, A-T has remained a clinical and molecular enigma. A-T is a multi-system disease inherited in an autosomal recessive manner, with a worldwide frequency of 1:100,000 live births and an estimated carrier frequency of 1% in the American population. Notable concentrations of A-T patients outside the United States are in Turkey, Italy and Israel.

Israeli A-T patients are Moroccan Jews, Palestinian Arabs, Bedouins and Druzes.

Cerebellar ataxia that gradually develops into general motor dysfunction is the first clinical hallmark and results from progressive loss of Purkinje cells in the cerebellum. Oculocutaneous telangiectasia (dilation of blood vessels) develops in the bulbar conjunctiva and facial skin, and is later accompanied by graying of the hair and atrophic changes in the skin. Somatic growth is retarded in most patients, and ovarian dysgenesis is typical for female patients. Among occasional endocrine abnormalities, insulin-resistant diabetes is predominant, and serum levels of alpha-fetoprotein and carcinoembryonic antigen are elevated. The thymus is either absent or vestigial, and other immunological defects include reduced levels of serum IgA, IgE or IgG2, peripheral lymphopenia, and reduced responses to viral antigens and allogeneic cells, that cause many patients to suffer from recurrent sinopulmonary infections.

Cancer predisposition in A-T is striking: 38% of patients develop malignancies, mainly lymphoreticular neoplasms and leukemias. But, A-T patients manifest acute radiosensitivity and must be treated with reduced radiation doses, and not radiomimetic chemotherapy. The most common cause of death in A-T, typically during the second or third decade of life, is sinopulmonary infections with or without malignancy.

The complexity of the disease is reflected also in the cellular phenotype. Chromosomal instability is expressed as increased chromosomal breakage and the appearance in lymphocytes of clonal translocations specifically involving the loci of the immune system genes. Such clones may later become predominant when a lymphoreticular malignancy appears. Primary fibroblast lines from A-T patients show accelerated senescence, increased demand for certain growth factors, and defective cytoskeleton structure. Most notable is the abnormal response of A-T cells to ionizing radiation and certain radiomimetic chemicals. While hypersensitive to the cytotoxic and clastogenic effects of these agents, DNA synthesis is inhibited by these agents to a lesser extent than in normal cells. The concomitant lack of radiation-induced cell cycle delay and reduction of radiation-induced elevation of p53 protein are evidence of a defect in a cell cycle checkpoint. Increased intrachromosomal recombination in A-T cells was also noted recently.

Prenatal diagnoses of A-T using cytogenetic analysis or measurements of DNA synthesis have been reported, but these tests are laborious and subject to background fluctuations, and therefore not widely used.

A-T homozygotes have two defective copies of the A-T gene and are affected with the disease. A-T heterozygotes (carriers) have one normal copy of the gene and one defective copy of the gene and, are generally healthy. When two carriers have children, there is a twenty-five percent risk in every pregnancy of giving birth to an A-T affected child.

A-T heterozygotes show a significant excess of various malignancies, with an 8-fold risk for all cancers between the ages of 20 and 80, and a 5-fold increased risk of breast cancer in women. These observations turn A-T into a public health problem and add an important dimension to A-T research, particularly to heterozygote identification. Cultured cells from A-T heterozygotes indeed show an intermediate degree of X-ray sensitivity, but the difference from normal cells is not always large enough to warrant using this criterion as a laboratory assay for carrier detection. Cytogenetic assays are labor intensive and not always consistent. The main reason for the unreliability of the previous assay methods is due to various degrees in overlap between A-T heterozygotes and non-heterozygotes with respect to radiosensitivity.

The nature of the protein missing in A-T is unknown. Cell fusion studies have established four complementation groups in A-T, designated A, C, D and E, suggesting the probable involvement of at least 4 genes or 4 types of mutations in one gene, with inter-allelic complementation. These four groups are clinically indistinguishable and were found to account for 55%, 28%, 14% and 3% of some 80 patients typed to date. In Israel, several Moroccan Jewish patients were assigned to group C, while Palestinian Arab patients were assigned to group A.

Therefore, in order to better understand the nature and effects of A-T as well as to more accurately and consistently determine those individuals who may carry the defective gene for AT, it would be advantageous to isolate the defective gene which is responsible for causing A-T and utilize this defective gene as a basis for detecting carriers of A-T and thereby be able to more beneficially manage the underlying conditions and predispositions of those carriers of the defective gene.

SUMMARY OF THE INVENTION AND ADVANTAGES

According to the present invention, a DNA clone derived from the defective gene which causes ataxia-telangiectasia (A-T), designated ATM, has been purified and isolated.

The present invention further includes the method for identifying carriers of the defective A-T gene.

BRIEF DESCRIPTION OF THE DRAWINGS

Other advantages of the present invention will be readily appreciated as the same becomes better understood by reference to the following detailed description when considered in connection with the accompanying drawings wherein:

FIGS. 1a–e illustrate the positional cloning steps to identify the A-T gene(s) wherein

DETAILED DESCRIPTION OF THE PREFERRED EMBODIMENT

The present invention consists of a DNA sequence of a cDNA clone, designated 7-9, derived from the defective gene responsible for ataxia-telangiectasia (ATM), as best shown in SEQ ID No:1, and cosmid clones containing the entire ATM gene DNA sequences flanking the gene as described in Savitsky et al. (submitted for publication) and incorporated herein by reference. The cDNA clone, designated 7-9, has been purified, isolated and cloned.

Mutations imparting defects into the A-T gene can be point mutations, deletions or insertions. The mutations can occur within the nucleotide sequence of either or both alleles of the ATM gene such that the resulting amino acid sequence of the ATM protein product is altered.

Table 1 illustrates several mutations in the 7-9 gene found in A-T patients.

| Patient[1] | Ethnic/ geographic origin | Complementation group[4] | Mutation mRNA sequence change | Protein alteration | Codon[9] | Patient's genotype[10] |
|---|---|---|---|---|---|---|
| AT2RO | Arab | A | Deletion of 11 nt[5] | Frameshift, truncation | 499 | Homozygote |
| AT3NG | Dutch | A | Deletion of 3 nt | Deletion, 1 residue[8] | 1512 | Compound heterozygote |
| AT15LA | Philippine | A | Insertion, +A | Frameshift, truncation | 557 | Compound heterozygote |
| AT3LA[2] AT4LA[2] | African-American | C | Deletion of 139 nt[6]/ Deletion of 298 nt[6] | Frameshift, truncation | 1196 | Compound heterozygotes |
| AT2BR | Celtic/Irish | C | Deletion, 9 nt | Deletion, 3 residues | 1198–1200 | Homozygote |
| AT1ABR | Australian | E | Deletion, 9 nt | Deletion, 3 residues | 1198–1200 | Homozygote |
| AT5BI[2] AT6BI[2] | Indian/English | D | Deletion, 6 nt | Deletion, 2 residues | 1079–1080 | Compund heterozygotes |
| F-2079[3] | Turkish | ND | Insertion, +C[5] | Frameshift, truncation | 504 | Homozygote |
| AT29AM | Italian | ND | Deletion of 175 nt | Frameshift, truncation | 132 | Homozygote |
| AT103LO | Canadian | ND | Insertion, +A | Frameshift, truncation | 1635 | Homozygote |
| F-596[3] | Palestinian Arab | ND | Deletion[7] | Truncation | Most of ORF | Homozygote |

[1]Cell line designation.
[2]Sibling patients' in both of whom the same mutation was identified.
[3]Patient expected to be homozygous by descent for an A-T mutation.
[4]According to Jaspers et al. (10). ND: not determined.
[5]An identical sequence change was observed in genomic DNA.
[6]No evidence for deletion was observed in genomic DNA. In both siblings, a normal mRNA was observed in addition to the two deleted species. The two deleted mRNAs may represent abnormal splicing events caused by a splice site mutation.
[7]Reflects a genomic deletion segregating with the disease in Family N. (FIG. 6).
[8]The deleted serine residue is located within the P13-kinase signature sequence (FIG. 4).
[9]Numbers refer to residue positions in FIG. 4.
[10]In all the compound heterozygotes, the second mutation is still unidentified.

Mutations in the ATM gene were found in all of the complementation groups suggesting that ATM is the sole gene responsible for all A-T cases.

In cloning the gene for A-T, the strategy used was a common strategy in identifying a disease gene with an unknown protein product known as positional cloning as is well known in the art. In positional cloning, the target gene is localized to a specific chromosomal region by establishing linkage between the disease and random genetic markers defined by DNA polymorphisms. Definition of the smallest search interval for the gene by genetic analysis is followed by long-range genomic cloning and identification of transcribed sequences within the interval. The disease gene is then identified among these sequences, mainly, by searching for mutations in patients.

Several important and long sought disease genes were isolated recently in this way (Collins, 1992; Attree et al., 1992; Berger et al., 1992; Chelly et al., 1993; Vetrie et al., 1993; Trofatter et al., 1993; The Huntington's Disease Collaborative Research Group, 1993; The European Polycystic Kidney Disease Consortium, 1994; Miki et al., 1994).

An A-T locus containing the A-T(A) mutations was localized by Gatti et al. (1988) to chromosome 11, region q22-23, using linkage analysis. The A-T(C) locus was localized by applicants to the same region of chromosome 11, region q22-23, by linkage analysis of an extended Jewish Moroccan A-T family (Ziv et al., 1991). Further studies, conducted by an international consortium of which applicant participated (McConville et al., 1990; Foroud et al., 1991; Ziv et al., 1992), reconfirmed this localization in a series of studies and gradually narrowed the A-T locus to an interval estimated at 4 centimorgan, which probably contains also the A-T(E) mutations.

Materials and Methods

Patient and family resources: A cell line repository was established containing to 230 patient cell lines and 143 cell lines from healthy members of Moroccan Jewish, Palestinian Arab and Druze families. Some of these pedigrees are highly inbred and unusually large (Ziv et al., 1991; Ziv, 1992). In view of the large number of meiotic events required for high-resolution linkage analysis, applicants collaborated with Dr. Carmel McConville (University of Birmingham, UK) and Dr. Richard Gatti (UCLA, Los Angeles, Calif.), who established extensive repositories of A-T families. Linkage analysis was conducted on a pool of 176 families.

Definition of the A-T interval by genetic analysis: Studies based only on analysis of Israeli A-T families enabled localization of the A-T(C) gene at 11q22-23 (Ziv, 1991), and confirmed the localization of A-T(A) mutation in Palestinians to the same region (Ziv et al., 1992). Studies with the Birmingham group further narrowed the major A-T interval to 4 centimorgans, between D11S611 and D11S1897 (McConville et al., 1993), and subsequently to 3 centimorgans, between GRIA4 and D11S1897 (Ambrose et al., 1994; McConville et al., 1994) (see also *Ataxia-Telangiectasis: Closer to Unraveling the Mystery*, Eur. J. Hum. Genet. (in press) and FIG. 1).

All these studies were conducted with biallelic markers, whose power is limited by their low polymorphic information content (PIC). The recently discovered microsatellite markers based on variable numbers of tandem simple repeats (Litt and Luty, 1989; Weber and May, 1989) are much more powerful due to their high degree of polymorphism. Microsatellite markers were used to saturate the A-T region using two approaches. The first, was based on physical mapping of microsatellite markers generated by others which were loosely linked to chromosome 11q.

Mapping experiments were conducted using YAC and cosmid contigs which allowed precise, high-resolution localization of DNA sequences in this region of chromosome 11. These experiments led to the localization of 12 microsatellites at the A-T region (Vanagaite et al., 1994a; Vanagaite et al., 1994b).

The second approach was based on generating new microsatellites within the YAC contig. A rapid method for the identification of polymorphic CA-repeats in YAC clones was set up (Rotman, 1994a) resulting in the generation of twelve new markers within the A-T locus (Vanagaite et al., 1994b; Rotman et al., 1994a; Rotman et al., 1994b). Hence, the high-density microsatellite map constructed in this manner contained a total of 24 new microsatellite markers and spans the A-T locus and flanking sequences, over a total of six megabases (Vanagaite et al., 1994b).

Figure 1:
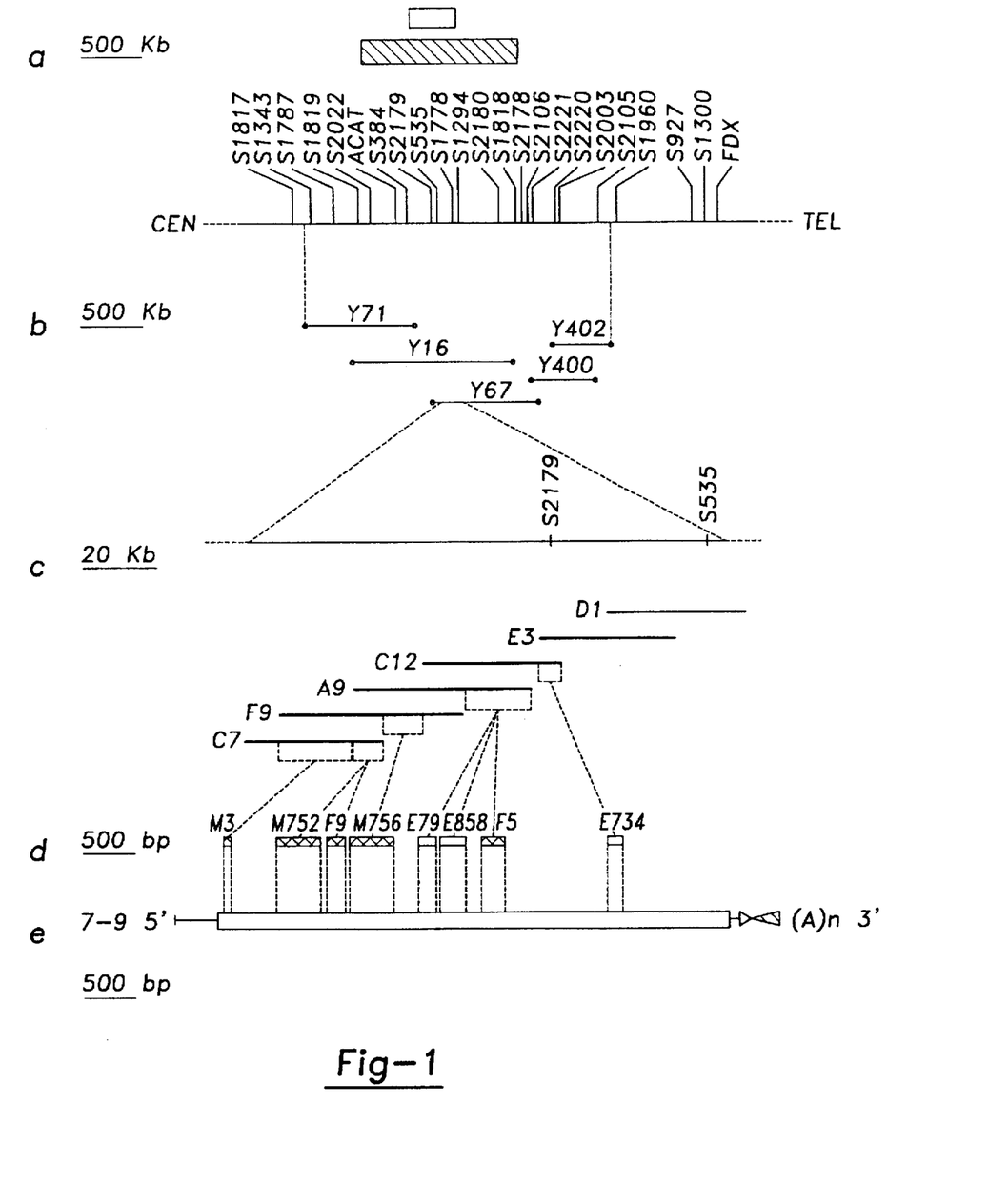
FIG. 1a is a high-density marker map of the A-T region on chromosome 11q22-23 (Kastan et al., (1992), constructed by generating microsatellite markers within genomic contigs spanning the region and by physical mapping of available markers using the same contigs, the prefix "D11" has been omitted from the marker designations, FDX: the adrenal ferredoxin gene, ACAT: the acetoacetyl-coenzyme A acetyltransferase gene, the stippled box denotes the A-T interval, defined recently by individual recombinants between the markers S1818 and S1819 in a consortium linkage study (Khanna and Lavin, 1993), the solid box indicates the two-lod confidence interval for A-T obtained in that study, between S1294 and S384.
FIG. 1b illustrates a part of a YAC contig constructed across this region (Beamish and Lavin, 1993)
FIG. 1c illustrates part of a cosmid contig spanning the S384-S1818 interval, generated by screening a chromosome-11 specific cosmid library with YAC clones Y16 and Y67, and subsequent contig assembly of the cosmid clones by physical mapping (Llerena et al., 1989)
FIG. 1d illustrates products of gene hunting experiments wherein solid boxes denote cDNA fragments obtained by using cosmid and YAC clones for hybrid selection of cDNAs (Swift et al., 1990, Heim et al., 1992) from a variety of tissues, open boxes denote putative exons isolated from these cosmids by exon trapping (Swift et al., 1990), these sequences hybridized back to specific cosmids (broken lines), which allowed their physical localization to specific subregions of the contig (dotted frames)
FIG. 1e illustrates a 5.9 kb CDNA clone, designated 7-9, identified in a fibroblast CDNA library (Shiloh et al., 1986) using the cDNA fragments and exons in id as a probe wherein open boxes denote an open reading frame of 5124 nucleotides, solid lines denote untranslated regions, striped arrowheads denote two Alu elements at the 3' end, and wherein dotted lines drawn between cDNA fragments and exons the cDNA indicate colinearity of sequences.

Repeated linkage analysis on the entire cohort of A-T families indicated that the A-T(A) locus was definitely located within a 1.5 megabase region between D11S1819 and D11S1818 (Gatti et al., 1994) as shown in FIG. 1 and in the review Shiloh et al. review article *Ataxia-Telangiectasis: Closer to Unraveling the Mystery*, Eur. J. Hum. Genet. (in press) with a clear peak of the cumulative lod score under D11S535 (Lange et al., 1994).

Concomitant with these studies, linkage disequilibrium (LD) analysis of Moroccan-Jewish A-T patients was conducted. LD refers to the non-random association between alleles at two or more polymorphic loci (Chakravarti et al., 1984). LD between disease loci and linked markers was a useful tool for the fine localization of disease genes (Chakravarti et al., 1984; Kerem, et al. 1989; Ozelius et al., 1992; Sirugo et al., 1992; Hastbacka et al., 1992; Mitchison et al., 1993). LD is particularly powerful in isolated ethnic groups, where the number of different mutations at a disease locus is likely to be low (Hastbacka et al., 1992; Lehesjoki et al., 1993; Aksentijevitch et al., 1993). Early on, applicants observed very significant LD ($p<0.02$-$p<0.001$) between A-T and markers along the D11S1817-D11S927 region in the patients of the sixteen Moroccan-Jewish A-T families identified in Israel (Oskato et al., 1993). Further analysis with the new markers narrowed the peak of linkage disequilibrium to the D11S384-D11S1818 region as shown in FIG. 1.

Haplotype analysis indicated that all of the mutant chromosomes carry the same D11S384-D11S1818 haplotype, suggesting a founder effect for A-T in this community, with one mutation predominating.

Long-range cloning of the A-T(A)/A-T(C) region: Cloning the disease locus in a contig (set of overlapping clones) was essential in isolating the A-T disease gene. The entire A-T locus and flanking region in a contig of yeast artificial chromosomes (YACs) was cloned by methods well known in the art (Rotman et al. 1994c; Rotman et al., 1994d). This contig was instrumental in the construction of the microsatellite map of the region (Vanagaite et al., 1994b) and subsequently enabled construction of cosmid contigs extending over most of the interval D11S384-D11S1818. Cosmids corresponding to the YAC clones were identified in a chromosome 11-specific cosmid library supplied by Dr. L. Deaven (Los Alamos National Laboratory) and were ordered into contigs by identifying overlaps as shown in FIG. 1.

Isolation of the A-T gene: Transcribed sequences were systematically identified based on two complementary methods:

1. Use of an improved direct selection method based on magnetic bead capture (MBC) of cDNAs corresponding to genomic clones (Morgan et al., 1992; Tagle, et al., 1993). In several, large-scale experiments YAC or cosmid DNA was biotinylated and hybridized to PCR-amplified cDNA from thymus, brain and placenta. Genomic DNA-cDNA complexes were captured using streptavidin-coated magnetic beads which was followed with subsequent elution, amplification, and cloning of captured cDNAs. YACs were also used and were no less efficient than cosmids as starting material for MBC, with more than 50% of the products mapping back to the genomic clones. However, when a small panel of radiation hybrids spanning the A-T region was used to test the cDNA fragments, it was found that some clones that hybridized back to the YACs and cosmids were not derived from this region. This pitfall probably stems from limited homology between certain portions of different genes, and points up the necessity to use radiation hybrid mapping when testing the authenticity of the captured sequences, and not to rely solely on cloned DNA for this purpose.

Homology searches in sequence databases showed that only one of the first 105 cDNA fragments mapped to the A-T region was homologous to a sequence previously deposited in one of the databases, as an expressed sequence tag (EST).

2. Exon amplification, also termed "exon trapping" (Duyk et al., 1990; Buckler et al., 1991), is based on cloning genomic fragments into a vector in which exon splice sites are flagged by splicing to their counterpart sites in the vector. This method of gene identification was expected to complement the MBC strategy, since it does not depend on the constitution of cDNA libraries or on the relative abundance of transcripts, and is not affected by the presence of repetitive sequences in the genomic clones. An improved version of this system (Church et al., 1993) that eliminated problems identified in an earlier version, including a high percentage of false positives and the effect of cryptic splice sites was utilized. Each experiment ran a pool of three to five cosmids with an average of two to five exons identified per cosmid. A total of forty five exons were identified.

Sequence analysis and physical mapping indicated that MBC and exon amplification were complementary in identifying transcribed sequences.

The availability of a deep cosmid contig enabled rapid and precise physical localization of the cDNA fragments and captured exons, leading to a detailed transcriptional map of the A-T region.

Both MBC and exon amplification yielded short (100–1000 bp) transcribed sequences. Those sequences were used as anchor points in isolating full-length clones from twenty eight cDNA libraries currently at applicants disposal and which represented a variety of tissues and cell lines.

Initial screening of the cDNA libraries by polymerase chain reaction (PCR) using primer sets derived from individual cDNA fragments or exons aided in the identification of the libraries most likely to yield corresponding cDNA clones.

Large scale screening experiments were carried out in which most of the cDNA fragments and exons were used in large pools. In addition to the mass screening by hybridization, PCR-based screening methods and RACE (rapid amplification of cDNA ends) (Frohman et al., 1988; Frohman et al., 1994) was employed to identify full-length cDNAs.

The above experiments resulted in the identification and isolation of a cDNA clone designated 7-9 (SEQ ID No:1) which is derived from a gene located under the peak of cumulative location score obtained by linkage analysis as shown in FIG. 1. The gene extends some 300 kilobases (kb) of genomic DNA and codes for two major MRNA species of 12 kb and 10.5 kb in length. The 7-9 clone is 5.9 kb in length and, therefore, is not a full length clone.

An open reading frame of 5124 bp within this cDNA encodes a protein with signature motifs typical of signal transduction proteins, most notably, phosphatidylinositol 3-kinases (PI 3-kinases). PI 3-kinases take part in the complex system responsible for transmitting signals from the outer environment of a cell into the cell. To date, it is not clear whether the protein produced from the 7-9 gene is a part of this transduction system or if it merely contains sequence motifs typical to signal transduction proteins.

The present invention further includes a recombinant protein encoded by the 7-9 gene. This recombinant protein is isolated and purified by techniques known to those skilled in the art.

Using the present invention, it is possible to transform host cells, including E. coli, using the appropriate vectors so that they carry either the native or recombinant DNA sequence of the 7-9 cDNA clone or a mutated sequence containing point mutations, deletions or insertions of DNA. Such transformed cells allow the study of the function and the regulation of the A-T gene. In particular, use of recombinantly transformed host cells allows for the study of the mechanisms of A-T, in particular, it will allow for the study of gene function interrupted by the mutations in the A-T gene region.

Recombinant methods known in the art can also be used to achieve the antisense or triplex inhibition of a target nucleic acid. For example, vectors containing antisense nucleic acids can be employed to express protein or antisense message to reduce the expression of the target nucleic acid and therefore its activity. Such vectors are known or can be constructed by those skilled in the art and should contain all expression elements necessary to achieve the desired transcription of the antisense or triplex sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses, DNA viruses, cosmids, plasmids, liposomes and other recombination vectors. The vectors can also contain elements for use in either procaryotic or eucaryotic host systems. One of ordinary skill in the art will know which host systems are compatible with a particular vector.

The vectors can be introduced into cells or tissues by any one of a variety of known methods within the art. Such methods can be found described in Sambrook et al., *Molecular Cloning: A Laboratory Manual*, Cold Springs Harbor Laboratory, New York (1992), in Ausubel et al., *Current Protocols in Molecular Biology*, John Wiley and Sons, Baltimore, Md. (1989), and include, for example, stable or transient transfection, lipofection, electroporation and infection with recombinant viral vectors., Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the antisense vectors to specific cell types in vivo or within a tissue or mixed culture of cells. Viral vectors can also be modified with specific receptors or ligands to alter target specificity through receptor mediated events.

A specific example of DNA viral vector for introducing and expressing antisense nucleic acids is the adenovirus derived vector Adenop53TK. This vector expresses a herpes virus thymidine kinase (TK) gene for either positive or negative selection and an expression cassette for desired recombinant sequences such as antisense sequences. This vector can be used to infect cells that have an adenovirus receptor which includes most cancers of epithelial origin as well as others. This vector as well as others that exhibit similar desired functions can be used to treat a mixed population of cells include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the anti-viral gancyclovir. Negative selection is therefore a means by which infection can be controlled because it provides inducible suicide through the addition of antibiotic. Such protection ensures that if, for example, mutations arise that produce altered forms of the viral vector or antisense sequence, cellular transformation will not occur. Features that limit expression to particular cell types can also be included. Such features include, for example, promoter and regulatory elements that are specific for the desired cell type.

Recombinant viral vectors are another example of vectors useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on desired cell type to be targeted. For example, if breast cancer is to be treated, then a vector specific for such epithelial cells should be used. Likewise, if diseases or pathological conditions of the hematopoietic system are to be treated, then a viral vector that is specific for blood cells and their precursors, preferably for the specific type of hematopoietic cell, should be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

If viral vectors are used, for example, the procedure can take advantage of their target specificity and consequently, do not have to be administered locally at the diseased site. However, local administration may provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with the appropriate target specificity for infection.

Transfection vehicles such as liposomes can also be used to introduce the non-viral vectors described above into recipient cells within the inoculated area. Such transfection vehicles are known by one skilled within the art.

The present invention includes the construction of transgenic organisms that are exhibit the phenotypic manifestations of A-T.

According to the present invention there is provided a method for diagnosing and detecting carriers of the defective gene responsible for causing A-T. Carrier detection is especially important since A-T mutations underlie certain cases of cancer predisposition in the general population. Identifying those carriers of the defective gene or missing or defective protein(s) encoded thereby, leads earlier and more consistent diagnosis of carrier of the A-T gene and, because carriers of the disease are more likely to be cancer-prone and/or sensitive to therapeutic applications of radiation, better surveillance and treatment protocols can be initiated. Conversely, exclusion of A-T heterozygotes from patients undergoing radiotherapy can allow for higher dose schedules than for other cancer patients thereby improving the efficacy of their treatment.

The method of carrier detection is carried out by first obtaining a sample of cells from a subject. Convenient methods for obtaining a cellular sample can include collection of either mouth wash fluids or hair roots. A cell sample could be amniotic or placental cells or tissue in the case of a prenatal diagnosis. A crude DNA could be made from the cells by techniques well known in the art. This isolated target DNA is then used for PCR analysis with appropriate primers derived from the gene sequence by techniques well known in the art. The PCR product would then be tested for the presence of appropriate sequence variations in order to assess genotypic A-T status of the subject.

In order to use the method of the present invention for diagnostic applications, it is advantageous to include a mechanism for identifying the presence or absence of target polynucleotide sequence. In many hybridization based diagnostic or experimental procedures, a label or tag is used to detect or visualize for the presence or absence of a particular polynucleotide sequence. Typically, oligomer probes are labelled with radioisotopes such as $^{32}P$ or $^{35}S$ (Sambrook pgs. 10.51–53) which can be detected by methods well known in the art such as autoradiography. Oligomer probes can also be labelled by non-radioactive methods such as chemilluminescent materials which can be detected by autoradiography (Sambrook pgs E.21–E.23) . Also, enzyme-substrate based labelling and detection methods can be used. Labelling can be accomplished by mechanisms well known in the art such as end labelling (Sambrook pg 10.51–10.55), chemical labelling, or by hybridization with another labelled oligonucleotide. These methods of labelling and detection are provided merely as examples and are not meant to provide a complete and exhaustive list of all the methods known in the art.

The introduction of a label for detection purposes can be accomplished by attaching the label to the probe prior to hybridization.

An alternative method for practicing the method of the present invention includes the step of binding the target DNA to a solid support prior to the application of the probe. The solid support can be any material capable of binding the target DNA, such as beads or a membranous material such as nitrocellulose or nylon. After the target DNA is bound to the solid support, the probe oligomers is applied.

The present invention also provides a kit for diagnosis and detection of the defective A-T gene. The kit includes a molecular probe complementary to genetic sequences of a defective gene which causes ataxia-telangiectasia (A-T) and suitable labels for detecting hybridization of the molecular probe and the defective gene thereby indicating the presence of the defective gene. The molecular probe having a DNA sequence complementary to sequences of 7-9 gene (SEQ ID NO:1).

Throughout this application various publications are referenced by citation or number. Full citations for the publications referenced by number are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Aksentijevitch et al., "Familial Mediterranean fever in Moroccan Jews: Demonstration of a founder effect by extended haplotype analysis" *Am. J. Hum. Genet.*, 53:644–651 (1993).

Ambrose et al., "A physical map across chromosome 11q22-23 containing the major locus for ataxia-telangiectasia. *Genomics*, 21:612–619 (1994).

Attree et al., "The Lowe's oculocerebrorenal syndrome gene encodes a protein highly homologous to inositol polyphosphate-5-phosphatase" *Nature*, 358:239–242 (1992).

Beamish and Lavin, "Radiosensitivity in ataxia-telangiectasia: anomalies in radiation-induced cell cycle delay" *J. Radiat. Biol.*, 65:175–184.

Berger et al., "Isolation of a candidate gene for Norrie disease by positional cloning" *Nature Genet.* 1:199–203, (1992)

Buckler et al., "Exon amplification: a strategy to isolate mammalian genes ased on RNA splicing" *Proc. Natl. Acad. Sci. USA*, 88:4005–4009 (1991).

Chakravarti et al., "Nonuniform recombination within the human beta-globin gene cluster" *Am. J. Hum. Genet.*, 36:1239–1258 (1984).

Chelly et al., "Isolation of a candidate gene for Menkes disease that encodes a potential heavy metal binding protein" *Nature Genet.* 3:14–19 (1993).

Church et al., "Isolation of genes from complex sources of mammalian genomic DNA using exon amplification" *Nature Genet.* 6:98–104 (1993).

Collins, F. S. "Positional cloning: let's not call it reverse anymore" *Nature Genet.*, 1:3–6 (1992).

Duyk et al., "Exon trapping: A genetic screen to identify candidate transcribed sequences in cloned mammalian genomic DNA" *Proc. Natl. Acad. Sci. USA*, 87:8995–8999 (1990).

Foroud et al. "Localization of the AT locus to an 8 cM interval defined by STMY and S132" *Am. J. Hum. Genet.*, 49:1263–1279 (1991).

Frohman, M. A. "On beyond classic RACE (rapid amplification of CDNA ends)" *PCR Methods and Applications*, 4:S40–S58 (1994).

Frohman et al., "Rapid production of full-length cDNAs from rare transcripts: Amplification using a single gene-specific oligonucleotide primer" *Proc. Natl. Acad. Sci. USA*, 85:8998–9002 (1988).

Gatti et al., "Genetic haplotyping of ataxia-telangiectasia families localizes the major gene to an 850 kb region on chromosome 11q23.1" *Int. J. Radiat. Biol.* (in press) (1994).

Gatti et al. "Localization of an ataxia-telangiectasia gene to chromosome 11q22-23" *Nature*, 336: 577–580 (1988).

Hastbacka et al., "Linkage disequilibrium mapping in isolated founder populations: diastrophic dysplasia in Finland" *Nature Genet.*, 2:204–211 (1992).

Heim et al., "Heterozygous manifestations in four autosomal recessive human cancer-prone syndromes" ataxia telangiectasia, xeroderma pigmentosum, Fanconi anemia, and Bloom syndrome" *Mutat. Res.*, 284:25–36 (1992).

Kastan et al., "A mammalian cell cycle checkpoint pathway utilizing p53 and GADD45 is defective in ataxia-telangiectasia" *Cell*, 71:587–597.

Kerem et al., "Identification of the cystic fibrosis gene: genetic analysis" *Science*, 245:1073–1080 (1989).

Khanna and Lavin, "Ionizing radiation and UV induction of p53 protein by different pathways in ataxia-telangiectasia cells" *Oncogene*, 8:3307–3312, (1993).

Lange et al., "Localization of an ataxia-telangiectasia gene to a 850 kb interval on chromosome 11q23.1 by linkage analysis of 176 families in an international consortium" (submitted) (1994).

Lehesjoki et al., "Localization of the EPM1 gene for progressive myoclonus epilepsy on chromosome 21: linkage disequilibrium allows high resolution mapping" *Hum. Mol. Genet.*, 2:1229–1234 (1993).

Litt and Luty. "A hypervariable microsatellite revealed by in vitro amplification of a dinucleotide repeat within the cardiac muscle actin gene" *Am. J. Hum. Genet.*, 44:397–401 (1989).

Llerena et al., "Spontaneous and induced chromosome breakage in chorionic villus samples: a cytogenetic approach to first trimester prenatal diagnosis of ataxia-telangiectasia syndrome" *J. Med. Genet.*, 26:174–178 (1989).

McConville et al., "Genetic and physical mapping of the ataxia-telangiectasia locus on chromosome 11q22-23" *Int. J. Radiat. Biol.* (in press) (1994).

McConville et al., "Paired STSs amplified from radiation hybrids, and from associated YACs, identify highly polymorphic loci flanking the ataxia-telangiectasia locus on chromosome 11q22-23" *Hum. Mol. Genet.*, 2:969–974 (1993).

McConville et al., "Fine mapping of the chromosome 11q22-23 region using PFGE, linkage and haplotype analysis; localization of the gene for ataxia telangiectasia to a 5cM region flanked by NCAM/DRD2 and STMY/CJ52.75, phi2.22" *Nucleic Acids Res.*, 18:4335–4343 (1990).

Miki et al. "A strong candidate for the breast and ovarian cancer susceptibility gene BRCA1" *Science*, 266:66–71 (1994).

Mitchison et al., "Fine genetic mapping of the Batten Disease locus (CLN3) by haplotype analysis and demonstration of allelic association with chromosome 16p microsatellite loci" *Genomics*, 16:455–460 (1993).

Morgan et al., "The selective isolation of novel cDNAs encoded by the regions surrounding the human interleukin 4 and 5 genes" *Nucleic Acids Res.*, 20:5173–5179 (1992).

Oskato et al., "Ataxia-telangiectasia: allelic association with 11q22-23 markers in Moroccan-Jewish patients. *43rd Annual Meeting of the American Society of Human Genetics*, New Orleans, La. (1993).

Ozelius et al., "Strong alleleic association between the torsion dystonia gene (DYT11) and loci on chromosome 9q34 in Ashkenazi Jews" *Am. J. Hum. Genet.* 50:619–628 (1992).

Parimoo et al., "CDNA selection: Efficient PCR approach for the selection of cDNAs encoded in large chromosomal DNA fragments" *Proc. Natl. Acad. Sci. USA*, 88:9623–9627 (1991).

Rotman et al., "Rapid identification of polymorphic CA-repeats in YAC clones" *Molecular Biotechnology* (in press) (1994a).

Rotman et al., "Three dinucleotide repeat polymorphisms at the ataxia-telangiectasia locus" *Human Molecular Genetics* (in press) (1994b).

Rotman et al., "A YAC contig spanning the ataxia-telangiectasia locus (groups A and C) on chromosome 11q22-23. *Genomics* (in press) (1994c).

Rotman et al., "Physical and genetic mapping of the ATA/ATC locus in chromosome 11q22-23" *Int. J. Radiat. Biol.* (in press) (1994d).

Savitsky et al., "A single gene with homologies to phosphatidylinositol 3-kinases and rad3+ is Mutated in all complementation groups of ataxiatelangiectasia" (submitted for publication).

Sirugo et al., "Friedreich ataxia in Louisiana Acadians: Demonstration of a founder effect by analysis of microsatellite-generated extended haplotypes" *Am. J.Hum. Genet.*, 50:559–566 (1992).

Shiloh, "Ataxia-telangiectasia: closer to unraveling the mystery" *European Journal of Human Genetics* (in press).

Shiloh et al., "Carrier detection in ataxia-telangiectasia" *The Lancet*, I:689 (1986).

Swift et al., "Cancer predisposition of ataxia-telangiectasia heterozygotes" *Cancer Genet. Cytogenet.*, 46:21–27 (1990).

Swift et al., "Incidence of cancer in 1616 families affected by ataxia-telangiectasia" *New Engl. J. Med.*, 325:1831–1836 (1991).

Tagle et al., "Magnetic capture of expressed sequences encoded within large genomic segments" *Nature*, 361:751–753 (1993).

The European Polycystic Kidney Disease Consortium, "The polycystic kidney disease 1 gene encodes a 14 ; kb transcript and lies within a duplicated region on chromosome 16" *Cell*, 77:881–894 (1994).

The Huntington's Disease Collaborative Research Group, "A novel gene containing a trinucleotide repeat that is expanded and unstable on Huntington's disease chromosomes" *Cell*, 72:971–983 (1993).

Trofatter et al., "A novel moesin-, ezrin-, radixin-like gene is a candidate for the neurofibromatosis 2 tumor suppressor" *Cell*, 72:791–800 (1993).

Vanagaite et al., "Physical localization of microsatellite markers at the ataxia-telangiectasia locus at 11q22-23. *Genomics*, 22:231–233 (1994a).

Vanagaite et al., "A high-density microsatellite map of the ataxia-telangiectasia locus" *Human Genetics* (in press) (1994b).

Vetrie et al., "The gene involved in X-linked agammaglobulinemia is a member of the src family of protein-tyrosine kinases" *Nature*, 361:226–233 (1993).

Weber and May, "Abundant class of human DNA polymorphisms which can be typed using the polymerase chain reaction" *Am. J. Hum. Genet.*, 44:388–396 (1989).

Ziv et al., "Ataxia-telangiectasia: linkage analysis in highly inbred Arab and Druze families and differentiation from an ataxia-microcephaly-cataract syndrome" *Hum. Genet.*, 88:619–626 (1992).

Ziv et al. "The ATC (ataxia-telangiectasia complementation group C) locus localizes to 11q22-q23.*Genomics*, 9:373–375 (1991).

---

I claim:

1. A purified, isolated and cloned DNA sequence consisting of a DNA sequence (SEQ ID No:1) partially encoding the gene, designated ATM, mutations in which cause ataxia-telangiectasia.

2. A purified, isolated and cloned DNA sequence according to claim 1 consisting of a cDNA sequence partially encoding the gene, designated ATM, mutations in which cause ataxia-telangiectasia (SEQ ID No:1).

3. The DNA sequence of SEQ ID No:1 altered by point mutations, deletions or insertions such that the resulting amino acid sequence is truncated imparting ataxia-telangiectasia.

4. A transformed *E. coli* carrying SEQ ID No:1.

5. A vector which comprises the DNA of claim 1.

6. A host cell, wherein the host cell is selected from the group of suitable eucaryotic and procaryotic cells, which is transformed with the vector of claim 5.

7. The host cell of claim 6 which is *E. coli*.

8. A vector which comprises the DNA of claim 3.

9. A host cell, wherein the host cell is selected from the group of suitable eucaryotic and procaryotic cells, which is transformed with the vector of claim 8.

10. The host cell of claim 9 which is *E. coli*.

11. A recombinant expression vector comprising a DNA sequence according to claim 1.

12. A recombinant expression vector according to claim 11 wherein the DNA sequence of SEQ ID No. 1 encodes a human phosphatidyllinositol 3-kinase or a biologically active derivatives thereof.

13. A method for detecting carriers of a defective ATM gene which causes ataxia-telangiectasia in families in which a patient with Ataxia-Telangiectasia has occurred, said method comprising the steps of:

obtaining a cell sample from a potential carrier;
isolating genetic material from the cell sample;
hybridizing the genetic material with molecular probes complementary to SEQ ID No:1 and point mutations, deletions or insertions thereof as found in the diagnosed Ataxia-Telangiectasia patient in order to detect carriers of the mutant gene; and
detecting the presence of the defective ATM gene which causes ataxia-telangiectasia thereby detecting the carriers.

14. A method as set forth in claim 13 wherein the genetic material isolated from the cell sample is DNA.

15. A method as set forth in claim 13 wherein the cell sample is blood.

16. A method as set forth in claim 13 wherein the cell sample is amniotic fluid.

17. A method as set forth in claim wherein the cell sample is placental cells.

18. A kit for detecting a defective gene causing ataxia-telangiectasia, said kit comprising:

a molecular nucleic acid probe complementary to SEQ ID No:1 and variants thereof and
detection means for detecting hybridization of said molecular nucleic acid probe and the defective ATM gene thereby indicating the presence of the defective ATM gene.

19. The DNA sequence of claim 3 further characterized by one of the deletions and insertions as set forth in TABLE 1.

20. The method as set forth in claim 13 wherein the deletions and insertions are as set forth in TABLE 1.

21. The kit as set forth in claim 18 wherein the variants are as set forth in TABLE 1.

* * * * *